United States Patent [19]

Bellofatto et al.

[11] Patent Number: 5,224,487
[45] Date of Patent: Jul. 6, 1993

[54] PORTABLE PEAK FLOW METER

[75] Inventors: Steven Bellofatto, Closter; M. Zubair Mirza, Wyckoff, both of N.J.

[73] Assignee: Healthscan Products, Inc., Cedar Grove, N.J.

[21] Appl. No.: 734,198

[22] Filed: Jul. 22, 1991

[51] Int. Cl.⁵ ............................................. A61B 5/087
[52] U.S. Cl. ................................. 128/725; 128/716; 128/200.24
[58] Field of Search ........................... 128/716–720, 128/726, 727, 730, 200.14, 200.24, 201.26, 725

[56] References Cited

U.S. PATENT DOCUMENTS

| | | |
|---|---|---|
| 2,467,923 | 4/1949 | Allen . |
| 2,965,111 | 12/1960 | Feigelman . |
| 3,298,362 | 1/1967 | Lippitt . |
| 3,749,087 | 7/1973 | Klohr ............................ 128/725 |
| 3,826,247 | 7/1974 | Ruskin . |
| 3,848,584 | 11/1974 | Otsap . |
| 3,848,585 | 11/1974 | Otsap . |
| 3,871,364 | 3/1975 | Boehringer . |
| 4,041,935 | 8/1977 | Garbe . |
| 4,703,853 | 11/1987 | Byrns . |
| 4,735,309 | 4/1988 | Nemeth . |
| 4,782,828 | 11/1988 | Burnett et al. ............... 128/200.14 |
| 4,834,083 | 5/1989 | Byram et al. ................ 128/200.14 |
| 4,944,306 | 7/1990 | Alvino . |
| 4,949,715 | 8/1990 | Brugger ......................... 128/200.14 |
| 4,953,545 | 9/1990 | McCarty ....................... 128/200.14 |
| 4,961,344 | 10/1990 | Rodder . |
| 4,969,455 | 11/1990 | Ramella ........................ 128/200.14 |
| 5,007,419 | 4/1991 | Weinstein et al. ............ 128/200.14 |
| 5,042,467 | 8/1991 | Foley ............................ 128/200.14 |
| 5,069,204 | 12/1991 | Smith et al. .................. 128/200.23 |
| 5,199,806 | 6/1992 | Palson et al. ................. 128/200.14 |

FOREIGN PATENT DOCUMENTS 2238389  5/1991  United Kingdom ............... 128/725

Primary Examiner—Lee S. Cohen
Assistant Examiner—K. M. Pfaffle
Attorney, Agent, or Firm—Schweitzer Cornman & Gross

[57] ABSTRACT

A portable peak flow meter for monitoring the expiratory flow rate of a user includes an on-line metering unit having a combination cover and handle. The metering unit, which has opposed mouthpiece and exit ends, is of generally rectangular construction. A pair of opposed and hinged cover elements are pivotly mounted to the side walls of the metering unit, and pivot from a first position in which they embrace and cover the mouthpiece, to a second position perpendicular to the length of the metering unit in which they serve as a handle. The cover elements both maintain the mouthpiece in a sanitary condition when the unit is not in use and allows the unit to be held in a manner where the user's hand is distanced from the meter, thus preventing interference with operation of the unit.

14 Claims, 4 Drawing Sheets

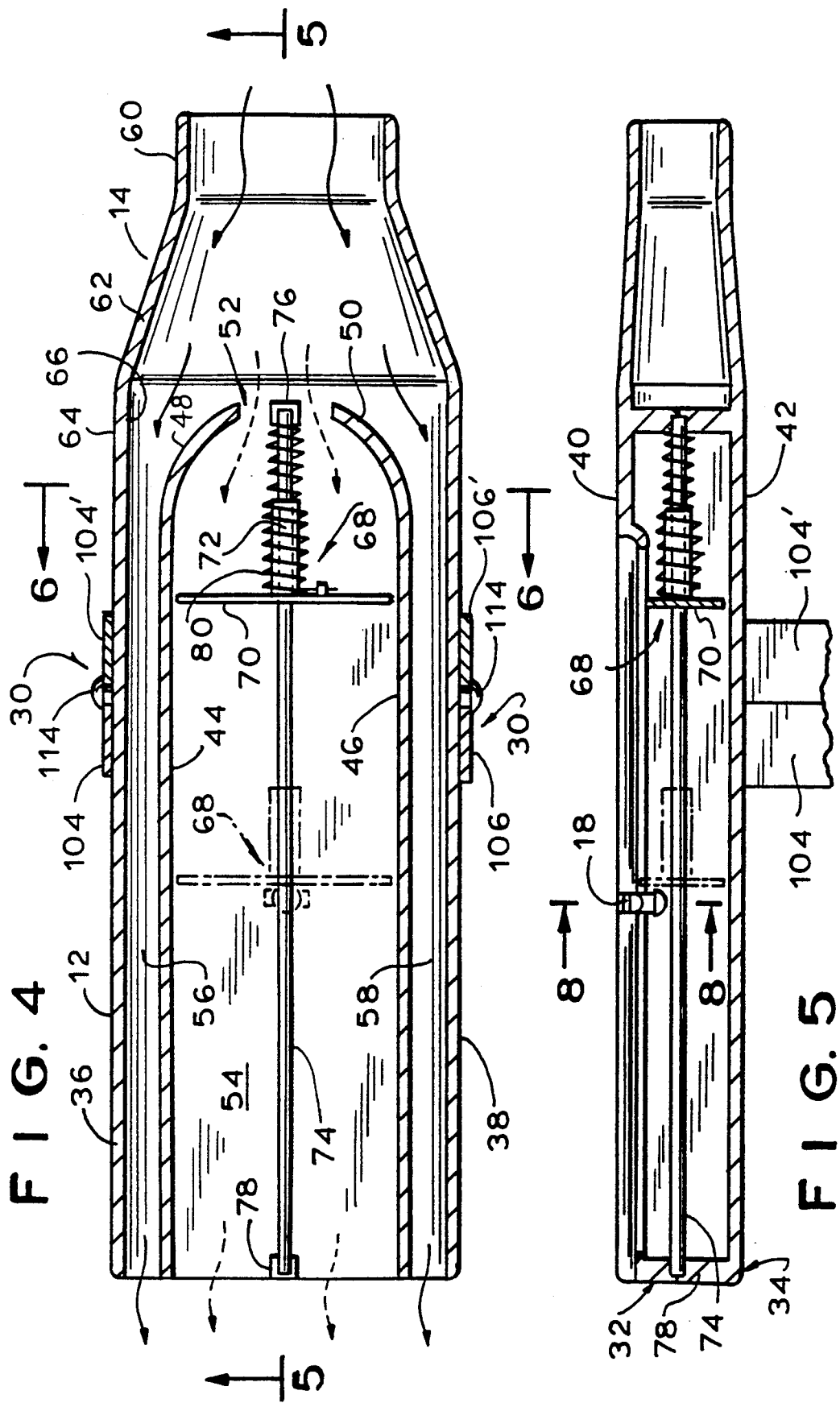

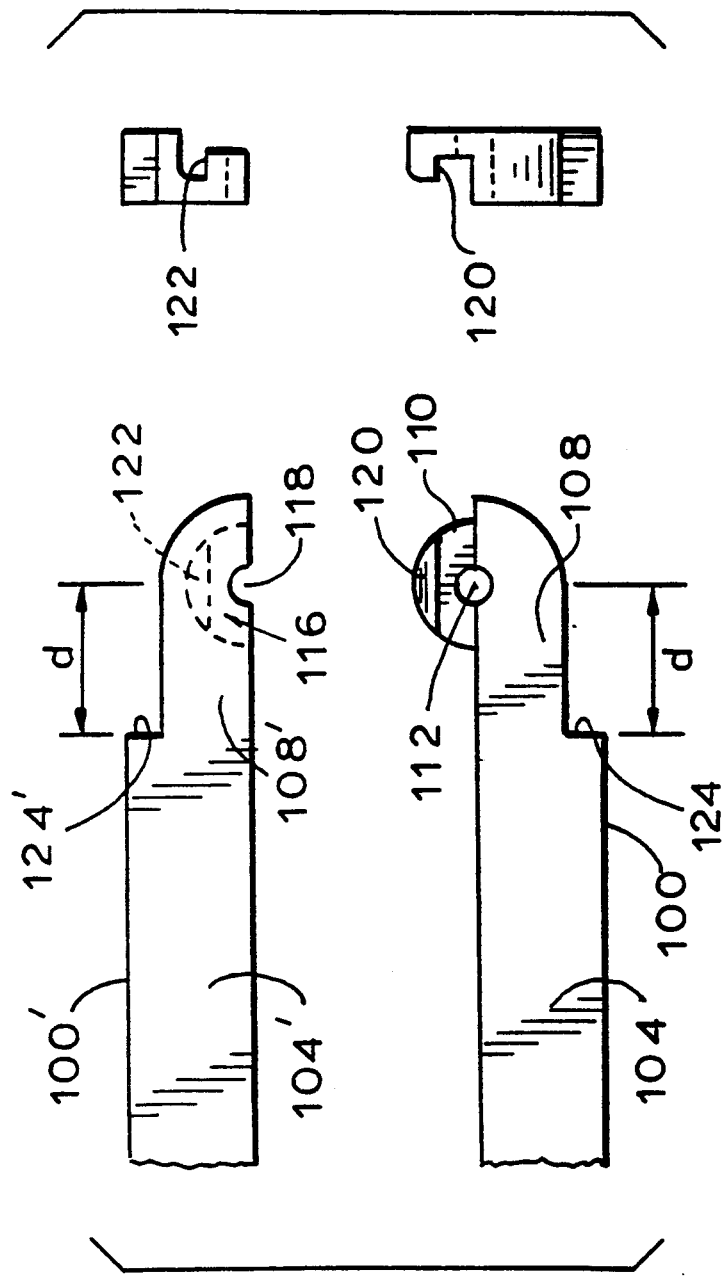

PORTABLE PEAK FLOW METER

The present invention relates to an expiratory flow rate measuring and monitoring device, and particularly to such a device which may be easily transported upon the person.

BACKGROUND OF THE INVENTION

It is well established that the measure of peak expiratory flow rate is a good indication of the condition of the airways of the body. Thus, such measurement is helpful, for example, in the management of asthma.

Asthma is recognized as a chronic disease which can manifest itself in bronchial inflammation of which the patient may be unaware, and has the ability to result in an acute attack under a variety of circumstances, resulting in the partial or complete obstruction of the breathing of the individual. Because of its chronic nature, asthma patients must be continuously on guard to become aware of symptoms which might forebode an attack. The use of effective anti-asthma drugs can substantially limit or eliminate such attacks, but need to be dispensed with care to prevent both over- and under-dosing.

An effective method for managing asthma is testing the respiratory function. Such testing may typically be performed by the patient himself by use of a portable peak expiratory flow meter. Such devices measure the peak expiratory flow rate, that is, the maximum rate of air flow which can be exhaled under various circumstances and at various times throughout the day. This permits the patient to monitor the respiratory function and receive warning of changes in respiratory function which may indicate an impending asthma attack.

Typically, such peak flow meters, even when characterized as "portable" are of relatively large size, and are not conducive to inconspicuous transport or use by the patient. The peak flow meter depicted in Alvino, U.S. Pat. No. 4,944,306, for example, utilizes a vertically-extending indicator tube affixed to a horizontal mouthpiece/exit port. While providing accurate peak flow rate measurement over a range of expiratory flows, such an apparatus is relatively large and cumbersome, and is not easily transported on the person. Such constructions limit the effectiveness and usefulness of such devices by impeding the ability of the patient to keep such a peak flow meter with him at all times so that respiratory rate can be monitored whenever required.

It is thus a purpose of the present invention to provide a peak flow meter of improved construction which results in a compact unit being able to be carried on the person.

Yet another purpose of the present invention is to provide a peak flow meter having the capacity to be folded into a compact unit for transit and being able to be unfolded into a use position.

Still another purpose of the present invention is to provide such a device in which the mouthpiece of the unit is protected from the environment when not in use, thus improving the sanitation and safety of the unit.

Yet a further purpose of the present invention is to provide such a device in a manner which may be efficiently and economically manufactured.

BRIEF DESCRIPTION OF THE INVENTION

In accordance with the foregoing and other purposes and objects, the present invention is directed to an improved portable peak flow meter which utilizes a direct, in-line flow path for the expired air. The airflow is divided into a plurality of streams, the first of which activates a peak flow indicator means. The remaining air streams bypass the indicator. In this manner, the indicator mechanism deals with a relatively small volume of air and thus may be made more sensitive to changes in peak flow rate The flow meter is of generally rectangular configuration, with a mouthpiece at a first end and an exhaust at the opposed second end. It includes a pair of joined "clamshell" cover elements which cover the mouthpiece portion of the unit when not in use, open to expose the mouthpiece, and pivot downwardly to an in-use position approximately perpendicular to the major axis of the flow meter where they provide an operating handle for the unit. In the "handle" position the user's left hand is maintained away from the body of the unit, thus insuring uninterrupted flow and non-interference with meter operation. After use the handle elements may again be pivoted to close about the mouthpiece, allowing the unit to be stored for subsequent use. The handle elements may preferably be joined by an integral "living" hinge for manufacturing nd eerformance efficiencies.

BRIEF DESCRIPTION OF THE DRAWINGS

A fuller understanding of the present invention will be accomplished upon consideration of the following detailed description of a preferred, but nonetheless illustrative embodiment of the present invention when reviewed in association with the annexed drawings, wherein:

FIG. 4 is a top plan view in section taken along line 4—4 of FIG. 1 detailing the interior of the invention;

FIG. 5 is a side elevation view in section taken along 5—5 of FIG. 4;

FIGS. 9A and 9B are detailed end and side elevation views, respectively, of the interconnection arms which join the covers to the body.

DETAILED DESCRIPTION OF A PREFERRED EMBODIMENT

Figure 1:
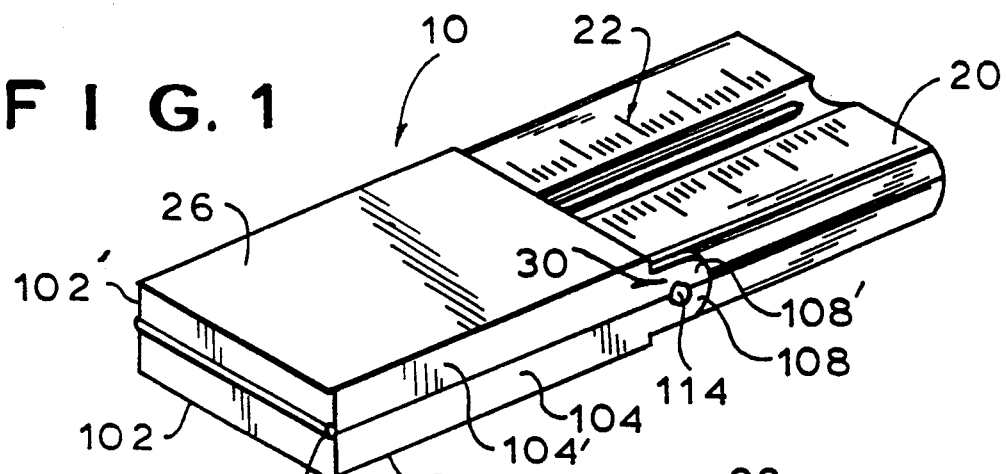
FIG. 1 is a perspective view of the present invention presented in the closed position with the handle elements covering the mouthpiece.
Figure 2:
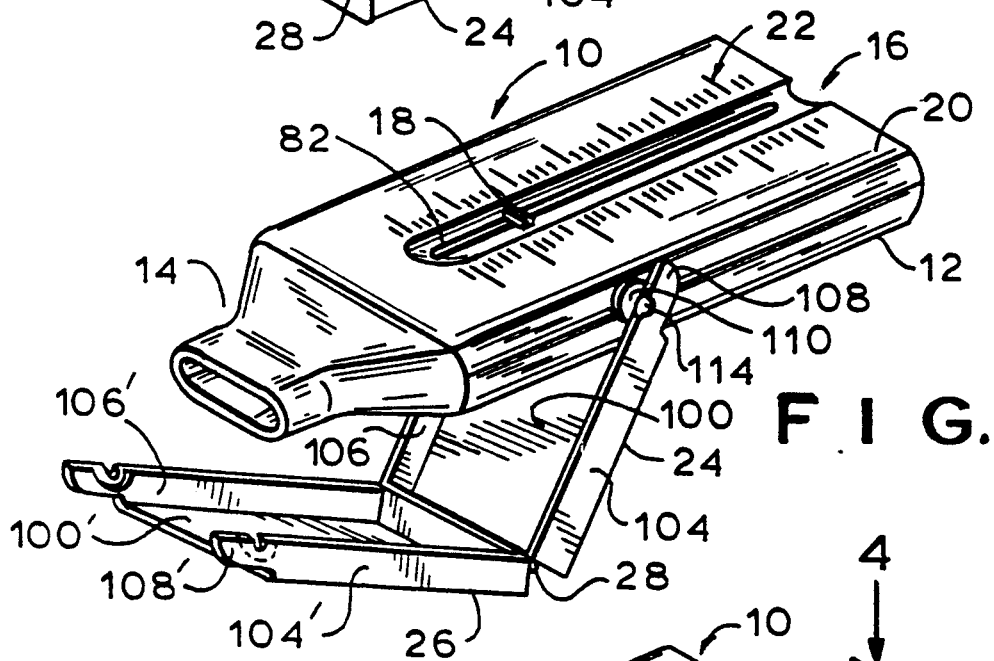
FIG. 2 is a perspective view showing the handle elements in a transitory position between the closed and open operating positions.
Figure 3:
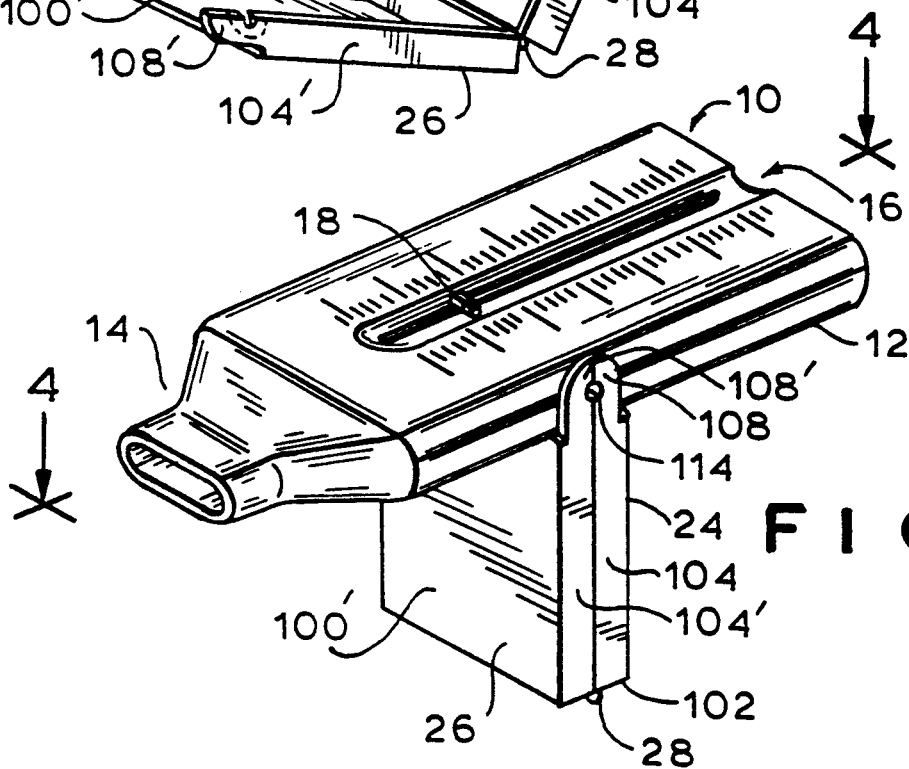
FIG. 3 is perspective view showing the invention in the fully open, operative position.

Referring initially to FIGS. 1 through 3, the portable peak flow meter 10 of the present invention consists of a main body 12 in the general form of a hollow rectangular prism, coupled to a mouthpiece 14 at a first end and having an exhaust at the opposed second end 16. A flow rate indicator 18 extends through a slot in the upper surface 20 of the body, which is provided with indicia 22 calibrated to indicate the flow rate shown by the indicator. A pair of cover elements 24, 26, hinged together at 28, are pivotly attached to the sides of the body at 30. In a first position, shown in FIG. 1, the cover pieces enclose the mouthpiece 14, while in the operating position as shown in FIG. 3, the cover elements 24, 26 extend downwardly from the body 12 in a generally perpendicular manner and provide an operating handle for the unit.

Figure 6:
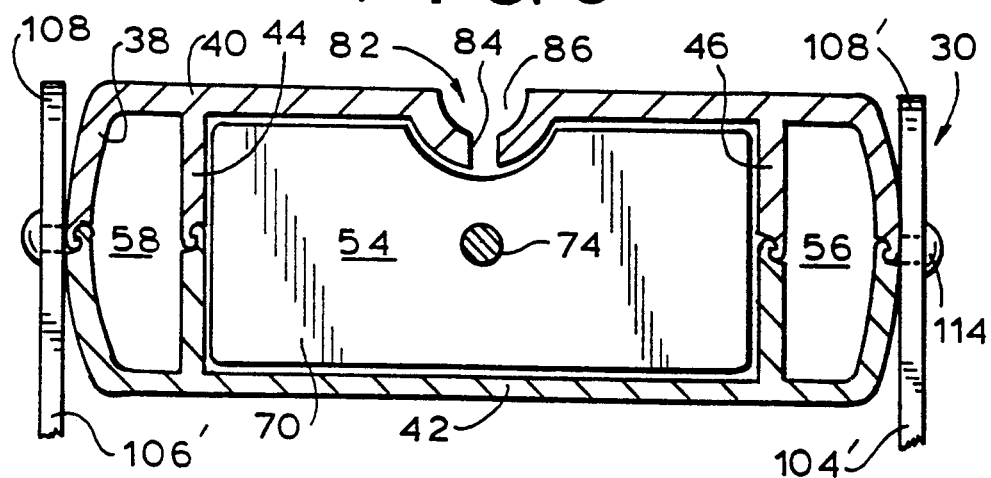
FIG. 6 is an end elevation view in section taken along line 6—6 of FIG. 4.
Figure 7:
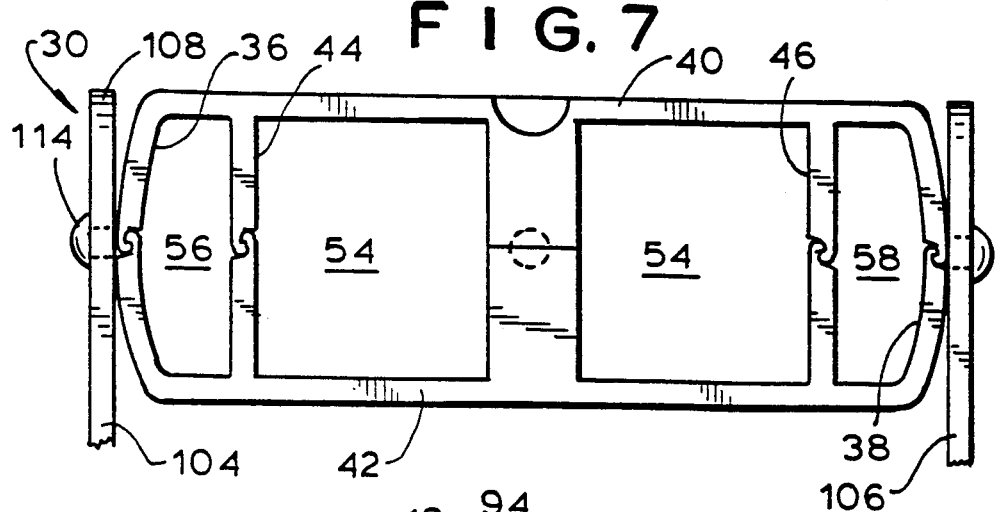
FIG. 7 is an end elevation view looking in from the right end of the unit as shown in FIG. 3.

With reference to FIGS. 4 through 6, the body 12 may be formed of upper and lower portions 32, 34, best seen in FIG. 5, which may be joined together along a horizontal seam in an appropriate manner to provide the body chamber. Interlocking elements may be provided to allow the portions to be joined together without the need for adhesive. As may be seen in FIG. 4, both upper and lower body portions include the opposed side walls 36, 38 which, in conjunction with top 40 on portion 32 and bottom 42 on portion 34 define a rectangular chamber through which the expired air passes.

Mounted within the chamber are interior walls 44, 46, each of which has portions formed as a part of upper body and lower body portions 32, 34. The interior walls divide the chamber into three generally parallel passageways 54, 56 and 58 having a common entrance port area at the right-hand end of the body. The inner walls 44, 46 include, at their proximal ends, respective arcuate portions 48, 50, the inwardly-directed ends of which define a narrow entrance aperture 52 into the central chamber 54. The arcuate portions 48, 50 also serve to smoothly divert the incoming air flow not aligned with the entrance aperture 52 to the opposed lateral passageways 56 and 58, defined by the side walls 36, 38 and the respective adjacent inner walls 44, 46.

Mouthpiece 14 adjoins the first end of the body 12 and includes a first portion 60 adapted and dimensioned to be held by the lips of the user, coupled to flared portion 62 which mates at its distal end with the first end of the body 12. As shown, the body 12 may be provided with a peripheral shoulder 64 which mates with a similar opposed shoulder 66 on the mouthpiece to connect the body and mouthpiece together. Both the body and mouthpiece may be formed of any appropriate material, such as styrene plastic. The mouthpiece may be permanently joined to the body or may be removable.

Mounted within central passageway 54 is piston 68, which the expiratory flow impinges against t provide measurement of its flow rate. As seen in FIGS. 4 and 5, piston 68 includes piston plate 70 positioned transversely to the passageway 54, and which provides a flow barrier across the passageway. The plate is mounted to collar 72, which has a bore therethrough through which support rod 74 extends, permitting travel of the piston along the length of the chamber. Support rod 74 is mounted at is ends in notched support blocks 76, 78, each of which is formed in two parts, as elements of the upper and lower body portions 32, 34 as may be seen in FIG. 5. Spring 80 has its first end affixed to the piston 68 and its second end affixed to the support block 76 at the entrance to passageway 54 to provide an appropriate restoring force against the force developed by the expirtory air against the piston plate 70.

In order to provide a visual indication of the maximum displacement of the piston 68 as a result of expiratory flow, the top 40 of the meter body is provided with a longitudinal slot 82 extending for a length corresponding to the travel of the piston from its rest position to a displaced position resulting from the maximum contemplated expiratory flow rate to be encountered.

Figure 8:
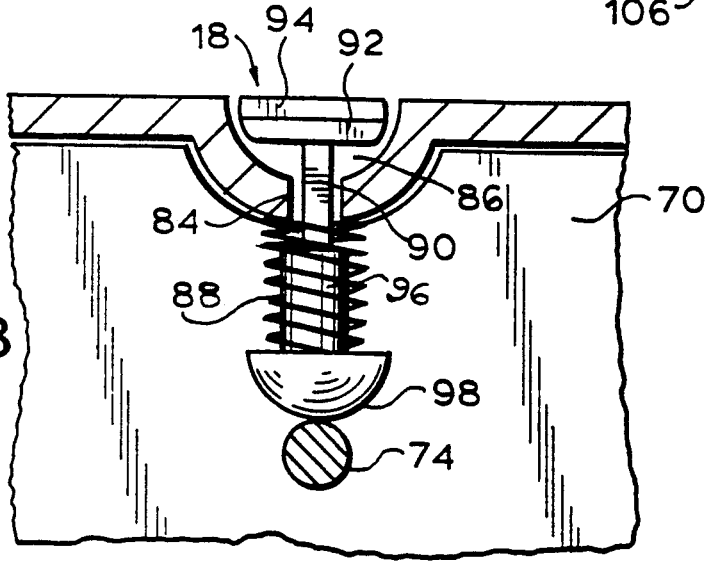
FIG. 8 is a detail elevation view in section taken along line 8—8 of FIG. 5 illustrating the indicator mechanism of the invention.

As may be seen in FIGS. 6 and 8, the slot 82 may include a lower neck portion 84 having parallel sides adjoining an upper, generally semicircular portion 86. Extending through the slot is the indicator 18, seen in FIG. 8, which includes a neck section 90 rectangular in cross-section adapted to be embraced by the neck section of the slot. The neck 90 supports at its upper end an indicator head 92 embraced by the hemispherical portion 86 of the slot, the head bearing on its top surface a transversely directed, generally rectangular pointer means 94 which, during travel, aligns with the indicia 22 seen in FIG. 3 to indicate the flow rate. Extending downwardly from the neck 90 is a widened base portion 96, terminating in hemispherical end 98. The hemispherical end 98 rests upon support rod 74 and is engaged by the piston plate 70 whereby the indicator is moved leftwardly as shown in FIGS. 4 and 5 in accordance with the maximum expiratory flow rate developed by the user. As the flow rate decreases, the piston returns to the right, the indicator remaining in its .position of maximum displacement from its initial, rightmost rest position to indicate the maximum flow. Frictional forces between the indicator and the top wall and/or the support rod 74 retain the indicator in position upon retraction of the piston. Spring means 88 encircling portion 96, provides an expansion force between the hemispheric end 98, top wall 40 and support rod to enhance the frictional contact to insure that the indicator does not inadvertently change position.

The cover pieces 24, 26 provide protection for the mouthpiece 14 of the device when not in use and, when pivoted to the position as shown in FIG. 3, both expose the mouthpiece for use and serve as an operating handle for the unit. As seen in FIGS. 1-3, first cover piece 24 includes a bottom panel 100 surrounded by upstanding end wall 102 and opposed side walls 104, 106. A pair of arms 108 are formed as extensions to the side walls 104, 106, each arm including a generally semicircular shoulder portion 110 of reduced thickness fully surrounding transverse bore 112, as detailed in FIGS. 9A and 9B. Posts 114 extend from the body side walls 36, 38, and serve as axles through the bores 112, allowing the handle unit to pivot thereabout. The portion of the post 114 extending beyond the bore may be widened or otherwise deformed to prevent removal of the handle.

The second cover piece 26 is of generally similar construction, including top panel 100', end wall 102' and side walls 104', 106'. Its arm portions 108' are each provided with a semicircular recess 116 on the inner face thereof to accept the semicircular shoulder 110 of the arm 108, and further includes semicircular transverse bore 118 to accommodate the posts 114.

The semicircular shoulders 110 of the arms 108 may further include a latch shoulder 120, which engages with a complimentary shoulder 122 formed into the surface of the semicircular recess 116 in the arms 108', such that the cover elements may interengage and lock, both in the closed position as shown in FIG. 1, as well as in the open and operative position as shown in FIG. 3. The cover portions 24, 26 may be formed from a unitary piece of material, typically polypropylene, and are joined at the tops of their end walls 102, 102' by integral self-hinge element 28. It is to be further appreciated that the distance "d" between the ends 124, 124' of the bottom and top panels 100, 100', respectively, and the center of the transverse bores 112, 118 in the respective arms 108, 108' is equal to the height above the bottom 42 of the body for the axis of posts 114, such that in the open position, as shown in FIG. 3, the handle assumes the perpendicular position, whereby the body 10 is generally retained in position by the ends 124, 124' of the cover panels.

The peak flow meter is normally disposed in the closed condition shown in FIG. 1, with the cover pieces 24, 26 engaged with each other about the mouthpiece of the unit. In such a condition, the unit may be placed in the pocket, in a handbag or attache case, or the like, with the mouthpiece being covered and protected from inadvertent contact with surrounding objects. When it becomes necessary to operate the device, the cover elements are separated and pivoted about the body, re-engaging in the perpendicular position as shown in FIG. 3. The piston is in the rest position as depicted in FIG. 4. The indicator is gently slid to the right such that the hemispheric protrusion 98 is in gentle contact with the piston. The user then places the mouthpiece in his or her mouth and exhales through the unit in the manner taught by the prescribing professional. The expiratory breadth enters the body of the unit, a substantial portion thereof being diverted by the curved end portions 48, 50 of the inner walls 44 and 46 to pass the piston through the lateral passageways 56, 58. A portion of the air enters the central air passageway 54, where it impinges against the piston plate 70, driving the piston plate to the left as shown in phantom in FIG. 4 against the restoring force of the spring 80. Slot 82 allows for dissipation of the breadth portion impinging against the piston without substantial diminution of the force generated thereby.

Maximum travel of the piston corresponds to the maximum flow rate and resultant force. As the flow rate decreases and terminates, the piston returns to the rest position. During piston travel, however, the indicator 18 is driven to the left, remaining in the position corresponding to the maximum flow rate. This maximum flow rate can be read off the indicia 22 on the top surface of the unit, the flow rate to be used for reporting or medication dispensation by the patient as instructed. The indicator then may be reset to the rightmost position, the handles being separated from the operative position to be refolded about the mouthpiece of the unit to permit storage.

In general, for a central passageway of cross-sectional area of 1.125 inches × 0.52 inches and having an entranceway of 0.375 inches by 0.52 inches, a spring formed of 0.008 inches diameter type 302 stainless steel having a spring constant of 0.0134 lb./inch has been found to allow measurement across the range of flow rates typically experienced with a piston travel of about 3.8 inches.

It is to be recognized that modifications and adaptations of the present invention as set forth herein are possible without departing from the spirit or scope of the invention.

We claim:

1. A breath flow meter comprising a hollow meter body; flow measurement means mounted in said body for measuring and displaying the flow rate of breath passing through said meter body; a mouthpiece at a first end of said body and a breath outlet in said body displaced from said first end; a cover coacting pivot means for pivotally mounting said cover to said body, and means for selectively maintaining said cover in a chosen one of two alternative orientations wherein a first orientation encloses said mouthpiece and a second orientation extends said cover from said body as a handle.

2. The apparatus of claim 1, wherein said meter body comprises a plurality of passageways therethrough between said mouthpiece and said breath outlet.

3. The apparatus of claim 2, wherein said flow measurement means is located in one of said passageways.

4. The apparatus of claim 3, further comprising means within said body for diversion of the breath among each of said passageways.

5. The apparatus of claim 1 wherein said measurement means includes indicator means adapted to retain a measurement of peak flow through said body.

6. A breath flow meter comprising an elongated hollow meter body having first and second ends and opposed side walls; flow measurement means for measuring and displaying flow rate of breath passing through the meter body mounted in said body; a mouthpiece at said first end; and first and second hinged, mating cover elements, at least one of said cover elements having means for pivotally mounting said cover elements to said body to selectively enclose or expose said mouthpiece.

7. The apparatus of claim 6, wherein said means for pivotally mounting said at least one of said cover elements comprises an axle post projecting from each of said opposed side walls, and a pair of opposed arms mounted to said first cover element, each of said arms including means for accepting said axle posts projecting from each of said opposed side walls.

8. The apparatus of claim 7, further comprising a self-hinge joining said cover elements.

9. The apparatus of claim 7, wherein said cover elements comprise fastening means to removably fasten them together to enclose said mouthpiece.

10. The apparatus of claim 9, wherein said fastening means for said cover elements comprise means for removably fastening said cover elements together to serve as a handle for said apparatus when said mouthpiece is exposed.

11. The apparatus of claim 7, wherein said means for pivotably mounting said cover elements includes means for removably fastening said cover elements together to serve as a handle for said apparatus while said mouthpiece is exposed.

12. The apparatus of claim 11, wherein said handle extends at an approximately right angle from said body.

13. A breath flow meter comprising an elongated hollow meter body having first and second ends and opposed side walls and being divided into a plurality of longitudinally-extending, flow-accepting passageways therein, said passageways having a common entrance port at said body first end; flow measurement means for measuring and displaying flow rate of breath passing through the meter body mounted within one of said passageways; a mouthpiece located at said body first end; a pair of cover elements; and pivot means for pivotally joining said cover elements to each other and to said body to allow said cover elements to alternatively enclose said mouthpiece and serve as a handle for the flow meter.

14. The apparatus of claim 13, wherein said measurement means comprise a spring-biased piston mounted for longitudinal travel in one of said passageways; a longitudinal slot in said meter body, and an indicator extending outwardly through said slot from said one of said passageways.

* * * * *

UNITED STATES PATENT AND TRADEMARK OFFICE
CERTIFICATE OF CORRECTION

PATENT NO. : 5,224,487
DATED : July 6, 1993
INVENTOR(S) : Steven Bellofatto

It is certified that error appears in the above-indentified patent and that said Letters Patent is hereby corrected as shown below:

```
Col. 2, line 18, delete "left";
       line 24, replace "nd eerformance" with
                        --and performance--.
```

Signed and Sealed this

Twentieth Day of December, 1994

Attest:

BRUCE LEHMAN

Attesting Officer

Commissioner of Patents and Trademarks